(12) United States Patent
Costa Ferrando et al.

(10) Patent No.: US 12,297,421 B2
(45) Date of Patent: May 13, 2025

(54) CELL CULTURE SYSTEM AND METHOD

(71) Applicant: AGLARIS LTD, Stevenage (GB)

(72) Inventors: Miquel Costa Ferrando, Stevenage (GB); David Horna Tomas, Stevenage (GB)

(73) Assignee: AGLARIS LTD, Stevenage (GB)

( * ) Notice: Subject to any disclaimer, the term of this patent is extended or adjusted under 35 U.S.C. 154(b) by 979 days.

(21) Appl. No.: 17/292,567

(22) PCT Filed: Nov. 7, 2019

(86) PCT No.: PCT/EP2019/080591
§ 371 (c)(1),
(2) Date: May 10, 2021

(87) PCT Pub. No.: WO2020/094809
PCT Pub. Date: May 14, 2020

(65) Prior Publication Data
US 2022/0002657 A1    Jan. 6, 2022

(30) Foreign Application Priority Data

Nov. 8, 2018 (EP) .................................. 18205113

(51) Int. Cl.
| C12M 1/36 | (2006.01) |
| C12M 1/00 | (2006.01) |
| C12M 1/12 | (2006.01) |
| C12M 1/34 | (2006.01) |

(52) U.S. Cl.
CPC ............ *C12M 41/48* (2013.01); *C12M 23/34* (2013.01); *C12M 25/02* (2013.01); *C12M 29/04* (2013.01); *C12M 29/10* (2013.01); *C12M 29/26* (2013.01); *C12M 41/34* (2013.01)

(58) Field of Classification Search
CPC ...... C12M 41/48; C12M 23/34; C12M 25/02; C12M 29/04; C12M 29/10; C12M 29/26; C12M 41/34
USPC ....................................................... 435/294.1
See application file for complete search history.

(56) References Cited

U.S. PATENT DOCUMENTS

| 5,017,490 A | 5/1991 | Taiariol et al. |
| 2015/0353896 A1 | 12/2015 | Bruninghaus et al. |
| 2016/0145563 A1* | 5/2016 | Berteau ................. C12M 41/48 137/15.01 |
| 2018/0057783 A1 | 3/2018 | Paidus et al. |
| 2021/0292696 A1* | 9/2021 | Martin .................. C12M 23/08 |

FOREIGN PATENT DOCUMENTS

WO    2018057769 A1    3/2018

* cited by examiner

*Primary Examiner* — Michael L Hobbs
*Assistant Examiner* — Lenora A Abel
(74) *Attorney, Agent, or Firm* — Kramer & Amado, P.C.

(57) ABSTRACT

The present invention relates to a fungible suspension cell culture device. In particular, the invention relates to a fungible device with a configuration which allows modifying the volume of the cell culture area by automatically transferring said cell culture between different cell culture chambers which have different volumes. Furthermore, the present invention provides a suspension cell culture system.

15 Claims, 6 Drawing Sheets

CELL CULTURE SYSTEM AND METHOD

OBJECT OF THE INVENTION

The present invention relates to a cell culture system. In particular, the invention relates to a system with a configuration which allows modifying the volume of the cell culture area by transferring said cell culture between different cell culture chambers which have different volumes. Furthermore, the present invention provides a cell culture method.

BACKGROUND OF THE INVENTION

The chemical or pharmaceutical industries, among others, have an interest in the production of certain cell products, for which purpose they need to have a number of bioreactors and manpower to assure a product with the highest quality, and the highest possible energy and resource optimization.

To obtain a desired product, it is of great importance to control that the cell culture processes are carried out in a suitable manner and under the best conditions for the cell culture, according to its different characteristics.

For a desired development and growth, the cells in suspension must be cultured in increasing volumes as the culture process progresses.

Different vessels of different sizes have conventionally been used for culturing cells contained in a culture medium. These conventional means, however, had different drawbacks.

Some of these drawbacks are:
Deficient or nonexistent quality control;
Impossibility of monitoring the state of the culture in real time;
Risk of contamination by contact with the external medium when manually transferring from one vessel to another of larger volume;
Need for thorough time control due to the rate of development of the culture;
Loss of product quality due to the cellular stress inflicted on the culture if the mentioned time requirement, which requires the change in volume at specific times of the suspension cell culture process, is not complied with;
Exponential increase in both time and manpower resources invested to optimize product quality complying with the requirements mentioned above.

There are currently various systems which seek to systematize the culture process to get around these drawbacks. Some of these systems incorporate solutions, such as performing the cell culture in a bag, which requires constant shaking to keep the cells in suspension. Furthermore, as an additional problem, it requires a series of prior actions so as to achieve seeding the cells, due to the fact that the starting volume is too large.

There are also other systems where cell passages or transfers are performed manually, compromising process scalability, and therefore final quality control of the product.

DESCRIPTION OF THE INVENTION

The present invention proposes a solution to the aforementioned problems by means of a cell culture system according to claim 1, and a method for culturing cells according to claim 14. Preferred embodiments of the invention are defined in the dependent claims.

A first inventive aspect provides a cell culture system, characterized in that it comprises:

a plurality of cell culture chambers configured for culturing therein cells contained in a culture medium, and configured for being in fluid communication with one another through a network of channels,
fluid flow rate control means for a fluid circulating through the network of channels,
culture medium conditioning means,
measurement means configured for monitoring the state of the culture medium and/or cells,
a controller in connection with the fluid flow rate control means and/or with the conditioning means, the controller being configured for being in data communication with the measurement means,
wherein
each cell culture chamber comprises a plurality of fluid inlets-outlets;
the plurality of cell culture chambers all comprise different internal volumes,
the controller, according to the data measured by the measurement means, is furthermore configured for:
operating the conditioning means, and/or
operating the fluid flow rate control means such that the cells contained in culture medium inside a first chamber are transferred to the inside of a second chamber the internal volume of which is larger than the internal volume of the first chamber, and so on, successively, were it necessary, to chambers with larger internal volume,
and wherein the system further comprises cell retention means configured for retaining cells inside the cell culture chambers.

Throughout this document, fluids are understood to mean liquid media and/or cells contained in liquid media. Several examples of fluids, such as culture media and/or cells contained in culture medium, are defined in the present invention. Furthermore, throughout the description, cell culture is understood to mean cells contained in a liquid medium, preferably culture medium. Likewise, the culture medium may be fresh culture medium, i.e., culture medium rich in nutrients and gases, or culture medium deficient in nutrients and gases. This distinction between culture media according to their amount of nutrients and gases is because the initial cells are initially contained in the initial culture medium (with the minimum of the nutrients and gases which allow performing the cell culture in optimal conditions) so that said cells can start to be cultured until achieving the desired end product (cultured cells). Throughout a suspension cell culture process carried out in the present systems, the culture medium can be replaced up to several times with a new one, or it can even be conditioned as many times needed for this culture medium to recover the gases required to continue to participate in the growth of the cells. This cell culture process is carried out between the different cell culture chambers comprised in the present systems.

The transfer of fluids between cell culture chambers is controlled by the actuation of the controller according to the data it receives from the measurement means. In other words, said transfer is performed through the action of the fluid flow rate control means for a fluid fluidically circulating throughout the network of channels. These fluid flow rate control means are also in charge of controlling the passage of initial or fresh culture medium and deficient culture medium throughout the network of channels, as well as the passage of the initial cells or the cells which are already cultured and contained in a culture medium. The fluid flow rate control means can be operated manually or automatically according to the features of the present systems. Nevertheless, the presence of the controller in systems allows the fluid flow rate control means and the conditioning means to be operated automatically when the systems determine that it is necessary.

The fluid inlets-outlets comprised in the cell culture chamber are understood to mean openings or entrances in said chamber through which fluids can be introduced and/or extracted. In a particular embodiment of any of the present systems, each cell culture chamber comprises at least one culture medium and/or cell culture inlet, and at least one culture medium and/or cell culture outlet. In another embodiment of any of the present systems, each cell culture chamber comprises a culture medium inlet, a cell culture or initial cell inlet, a culture medium outlet, and a cell culture or cultured cell outlet.

The main objective of the present invention is to provide a system suitable for culturing cells contained in a culture medium in an optimal manner. To that end, it is necessary for the cells to be kept confined in an enclosure, vessel, or chamber having certain volumetric characteristics that do not conform to the needs of the culture at that particular point of the cell culture process. As a result, the present system is equipped with a plurality of chambers communicated with one another, the internal volume of which increases according to culture process needs. In other words, as the cells become cultured, they gradually need a larger volume in order to expand and grow, and to that end they are transferred from one chamber to another chamber with a larger internal volume, and so on, successively, until the cell culture process ends. During cell culture, these cells are contained in culture medium inside the chamber and distributed over the entire extension allowed by surface of the base of the chamber. In a particular example in which the cells are suspended in culture medium inside the chamber, due to the effect of gravity these cells tend to be suspended in culture medium over the base surface of the cell culture chamber.

A further object of the present system is to provide means so that a cell culture is performed, in an optimal and automatic manner, through the transfer of cells between chambers when the controller so determines according to the data monitored by the measurement means. Additionally, another object is to prevent the cells from getting out of the cell culture chambers before the controller determines the transfer of said cells or, directly, their extraction as an end product.

In a particular embodiment, the plurality of cell culture chambers all comprise different base surface sizes, wherein the controller, according to the data measured by the measurement means, is configured for operating the fluid flow rate control means such that the cells contained in culture medium inside a first chamber are transferred to the inside of a second chamber the base surface of which is larger than the base surface of the first chamber.

The culture medium will be circulating through each cell culture chamber in which the cells are contained for the time required until they have to be transferred to a chamber of a larger internal volume. This circulation of culture medium is understood to mean that the culture medium is extracted from and introduced inside the chamber or chambers in a continuous manner or in intervals. This advantageously means that the deficient culture medium is extracted from the inside of the chamber, together with the waste generated by the cell during culture, and fresh or conditioned culture medium is introduced into the chamber so that it may provide the necessary gases to the cells in order to continue with their culture. In other words, the circulation of culture medium contributes to nutrients and gases being provided to the cells, as well as to the elimination of waste generated by the cells during their culture.

So that during the circulation of culture medium the flow of this culture medium that is being created does not entrain the cells and extract them from the inside of the chamber sooner than required, the system proposes cell retention means configured for retaining cells inside the cell culture chambers. Advantageously, these cell retention means retain the cells inside the cell culture chamber without the risk of them being entrained by the culture medium flow. The cells are retained inside said cell culture chamber until the controller operates the flow rate control means which allow the cells to be transferred to a chamber with a larger internal volume than the chamber in which they are located or to be extracted as the end product (cultured cells).

In a particular embodiment, the fluid flow rate control means comprise means for driving fluids which allow extracting and providing culture medium and/or cell culture, in a constant manner or in intervals, to the inside of the cell culture chambers. More particularly, the means for driving fluids throughout a network of channels can be peristaltic pumps or centrifugal pumps.

In a particular embodiment, the fluid flow rate control means comprise pinch valves regulating the passage of fluid through the network of channels.

The conditioning means comprised in the present systems are configured for providing to the deficient culture medium gases which have been lost (i.e., gases which have already been absorbed by the cells), to thereby advantageously recover their cell culture feeding capacity.

The measurement means are configured for monitoring the state of the culture medium and/or cells, and furthermore configured for being in data communication with the controller. Therefore, according to the data which the controller receives, the controller determines the needs of the cell culture and operates the fluid flow rate control means and/or conditioning means.

The fluid flow rate control means can be operated manually manual, i.e., when the user so desires, or automatically, i.e., through the controller according to the data monitored by the measurement means.

The measurement means, such as a sensor, for example, are in charge of monitoring the state of the cell culture or its components during the cell culture process in the present system. The present system further comprises a controller which will be in charge of operating the fluid flow rate control means and the conditioning means automatically according to the data sent by the sensor. The controller is configured, according to the measurements it receives from the sensor, for determining different actions on the cell culture, such as, for example, determining when the culture medium must be conditioned, or when it must be discarded and when it would therefore be necessary to introduce a new culture medium, or determining when the cells must be transferred to a chamber of a larger dimension. Depending on what the sensor measures in the culture medium, said sensor sends data in a continuous manner to the controller so that it can operate both the fluid flow rate control means and the conditioning means automatically. Nevertheless, a cell culture process can advantageously be carried out automatically, i.e., without the need for the user to continuously have to be vigilant and intervene with the components of the system.

The data regarding the state of the culture medium measured by the measurement means and sent to the controller authorize cells to be transferred between cell culture chambers as well as the number of times the conditioning means are operated or the circulation of the culture medium is changed.

Advantageously, the measurement means monitor in real time the state of the cell culture and/or cells during the cell culture process, and they furthermore allow the system to act automatically, i.e., without the user having to operate the components of any of the systems or handle the transfer of the content of the cell culture chambers.

To determine whether or not the culture medium continues to be suitable for culturing the cells, the measurement means monitor the amount of $O_2$ gas, $CO_2$ gas, and the pH of the culture medium, as well as also monitor the amount of glucose and lactate nutrient concentration, the biomass, and other metabolites.

In a particular embodiment, the cell retention means comprise filtration means arranged inside the cell culture chambers and being configured for filtering the culture medium and retaining the cells inside each cell culture chamber.

These filtration means arranged inside each cell culture chamber allow the passage of the culture medium therethrough while they retain the cells inside the chamber, i.e., they do not allow the passage of the cells therethrough. The filtration means advantageously retain the cells inside the cell culture chamber without the risk of them being entrained by the culture medium flow that is circulating through the fluid inlets-outlets during the culture medium circulation phases.

In a particular embodiment, the filtration means of at least one of the cell culture chambers comprises a filter membrane splitting said cell culture chamber into a first compartment suitable for containing therein a culture medium, and a second compartment suitable for containing therein cells contained in a culture medium,
wherein the filter membrane is configured for allowing the passage of the culture medium between both compartments and for retaining the cells in the second compartment.

The arrangement of two compartments inside the cell culture chamber, separated from one another by a filter membrane, allows the dissemination of the nutrients between the fresh culture medium entering the first compartment and the culture medium contained in the second compartment to take place during the circulation of culture medium in the first system, thereby balancing out the two culture media, i.e., the circulating medium and the medium contained in the cell culture chamber. Necessary nutrients are thereby provided to the cells, and waste generated by the cell, such as lactate, for example, is gradually eliminated since this waste is entrained by the culture medium exiting the cell culture chamber. The dissemination of nutrients between both compartments occurs as a result of the filter membrane which allows the culture medium to circulate between both compartments, being filtered through said membrane.

In a particular embodiment, each compartment comprises at least one fluid inlet-outlet.

The fact that the filter membrane splits the inner enclosure of the cell culture chamber into two compartments advantageously allows confining the cells contained in culture medium in one of the compartments, whereas the inflow of fresh culture medium and the outflow of deficient culture medium take place in the other compartment. In a particular embodiment, the first compartment is suitable for containing culture medium in continuous fluid communication with the inside of the second compartment through the filtration means. Particularly, the first compartment comprises a culture medium inlet and outlet. Advantageously, separating the culture medium inlet and outlet from the second compartment containing the cells contained in culture medium, prevents currents or turbulences generated by the throughflow of the culture medium entering and exiting the inside of the chamber from affecting the state of said cells.

In a particular embodiment, the first compartment comprises a plurality of walls defining between one another at least one culture medium distribution channel, wherein this culture medium distribution channel is connected along its entire extension to the filter membrane and to at least one fluid inlet-outlet of this first compartment.

Advantageously, the purpose of the channeling structure defined by the walls forming at least one distribution channel is so that said distribution channel covers the entire surface of the membrane. In other words, the culture medium entering the first compartment being circulated along the entire surface of the filtration means (filter membrane) is accomplished with this arrangement of walls. Therefore, when fresh culture medium is introduced in the first compartment through a fluid inlet, this fresh culture medium will travel the entire extension of the first compartment, thereby assuring that it sweeps the entire surface of the filter membrane along the way, and, therefore, the surface for exchanging nutrients and gases with the second compartment comprising the cells contained in culture medium is advantageously maximized. Furthermore, the plurality of walls allows the nutrients to be distributed homogenously.

In a particular embodiment, the culture medium distribution channel defined by the plurality of walls comprises a first end connected with a culture medium inlet and a second end connected with a culture medium outlet.

In a particular embodiment, the first compartment has an internal volume that is smaller than internal volume of the second compartment.

Advantageously, the volume available in the second compartment will be maximized in order to house the larger volume of cells contained in the culture medium. Advantageously, the residence time of the culture medium deficient in nutrients in the first compartment is also reduced, thereby accelerating its renewal, because it is either replaced with a new, fresh culture medium, or it is conditioned.

In a particular embodiment, the filtration means of at least one of the cell culture chambers comprises at least one filter arranged in at least one of the fluid inlets-outlets of the cell culture chamber. This filter is configured for allowing the passage of the culture medium through same and retaining the cells inside the chamber. In a particular example, the filter can be configured so as to allow retaining cells and cytokines, which are in the culture medium, inside the chamber. The concentration required throughout the entire culture medium would thereby decrease, given that there would be concentrates inside the chamber.

Advantageously, the presence of filters in the fluid inlets-outlets of the cell culture chamber allows these filters to be replaced with new ones without invading the inside of the cell culture chamber itself.

In a particular example, the retention means comprise a pump configured for circulating culture medium through the chambers at a pre-determined speed and with a flow direction at a first height with respect to a base of the chamber, this first height being greater than a second height at which the cells contained inside the chamber are arranged with respect to the base of the chamber, such that when the culture medium is circulated through the inside of the chamber, the cells are prevented from being entrained out of this cell culture chamber sooner than required.

The speed at which the culture medium is pumped into the cell culture chamber is pre-determined according to the size of the base surface of the cell culture chamber. In other words, the flow rate per surface unit at which the culture medium is introduced into the cell culture chamber is defined according to the size of the base surface of the chamber. The larger the surface is, the higher the culture medium flow rate is, i.e., the larger the base surface of the chamber is, the higher the flow rate that the cells contained inside the chamber can withstand. Furthermore, the culture medium flow rate will depend on the data measured by the means sensing the state of the cell culture, i.e., the culture medium flow rate may vary depending on the needs of the cells to be cultured.

The culture medium is driven by a pump that can be regulated into the cell culture chamber such that it enters and circulates through the inside of said cell culture chamber with a flow or circulation direction. That is, when the cells are introduced inside the cell culture chamber, due to the effect of gravity, the cells area contained in culture medium over the base surface of the cell culture chamber, at a second height above said base of the cell culture chamber. However, the culture medium is pumped into the cell culture chamber with a flow direction inside the chamber which is located at a first height with respect to the base of the chamber. The first height of the flow direction of the culture medium is greater than the second height where the cells contained in the cell culture chamber are located. Therefore, the pre-determined speed at which the culture medium is driven into the cell culture chamber is such that the culture medium flow originating inside the culture chamber does not entrain the cells and extract them from inside the chamber. As a result, the speed at which the culture medium enters the chamber as well as the arrangement of the cells below the flow direction of the culture medium is such that it prevents this flow direction of this culture medium from being perpendicular to the cells which thereby prevents the cells from being mixed and turbulences that may entrain the cells out of the chamber sooner than expected from being generated. In a particular embodiment, the cells are arranged inside the culture chamber contained in culture medium in several rows, such that the plurality of cells are arranged at different second heights, but all of them always below the flow direction of the culture medium circulating through the inside of the cell culture chamber.

The pump is configured so that the user may regulate the culture medium flow rate for pumping, as well as the speed thereof depending on the needs of the cell culture. In a particular embodiment, this pump can be a peristaltic pump, or a centrifugal pump, or a differential pressure pump. In a particular embodiment, the pump is configured for being automatically regulated by the controller depending on the needs of the cell culture.

The introduction of culture medium with a pre-determined speed and with a flow or circulation direction originates inside the cell culture chamber two spaces in fluid communication with one another. A first space is where the cells contained in culture medium are in an approximately steady state and distributed over the base surface of the chamber at the second height with respect to this base surface; and a second space is where the culture medium circulating at a first height with respect to the base surface of the cell culture chamber is located. Accordingly, a dissemination of nutrients between both spaces is originated due to the difference of concentrations between said spaces. This dissemination of nutrients between the culture medium circulating through the inside of the chamber and the cells contained in culture medium is what is responsible for maintaining the same concentration of nutrients between the first space and the second space.

The cells are retained inside said cell culture chamber until the controller operates the flow rate control means which allow the cells to the transferred to a chamber with an internal volume that is larger than the one in which they are located or to be extracted as an end product (cultured cells).

The circulation of culture medium inside the chamber advantageously provides the dissemination of nutrients between the fresh culture medium entering the culture chamber and the culture medium already contained in it, thereby balancing out the two culture media, i.e., the circulating medium and the medium contained in the cell culture chamber. Necessary nutrients are thereby provided to the cells, and the waste generated by the cell is gradually eliminated since this waste is entrained by the culture medium exiting the cell culture chamber. The dissemination of nutrients inside the culture chamber occurs as a result of the circulation of the fresh culture medium at a pre-determined speed and with a flow direction which is originated above same with respect to the base of the cell culture chamber.

The fact that the cells are approximately in a steady state due to the circulation of the culture medium at a pre-determined speed and are arranged below the flow direction of the culture medium mean that the system advantageously allows confining the cells contained in culture medium inside the chamber, whereas the inflow of fresh culture medium and outflow of deficient culture medium take place due to the circulation of culture medium. Furthermore, the speed and direction of the flow of the culture medium is such that it prevents currents or turbulences generated by the through-flow of the culture medium entering and exiting the inside of the chamber from affecting the state of said cells.

In a particular embodiment, each chamber comprises a plurality of walls defining between one another at least one culture medium distribution channel, wherein this culture medium distribution channel is connected to at least one fluid inlet-outlet.

Advantageously, the plurality of walls allows the nutrients to be distributed homogenously.

In a particular embodiment, the culture medium distribution channel comprises a first end connected with a culture medium inlet and a second end connected with a culture medium outlet.

In one embodiment, the conditioning means comprise a conditioning chamber configured for containing gases therein, the conditioning chamber being connected to the cell culture chambers through a gas-permeable membrane.

In another particular embodiment, the culture medium conditioning means comprise:

a conditioning chamber connected to the network of channels and configured for housing culture medium therein, and means for injecting at least one gas into the conditioning chamber.

Advantageously, these means for injecting gases into the culture medium provide to said culture medium the gases which were previously absorbed by the cells during the culture thereof.

In a more particular embodiment, the cell culture chamber is arranged inside the conditioning chamber such that the compartment of the cell culture chamber in which the cells contained in culture medium are stored comprises a gas-permeable (not liquid-permeable) membrane.

In another particular embodiment, the conditioning means comprise a gas-permeable, but not liquid-permeable, silicone tube arranged inside the cell culture chamber in the compartment where the cells contained in culture medium are stored.

In a particular embodiment, the system comprises:

a culture medium reservoir connected to the network of channels and configured for being in fluid communication with the inside of the cell culture chambers, and/or an initial cell reservoir connected to the network of channels and configured for being in fluid communication with the inside of the cell culture chambers, and/or a residue reservoir connected to the network of channels and configured for housing therein residual fluids coming from the inside of cell culture chambers, and/or an end product reservoir connected to the network of channels and configured for being in fluid communication with the inside of the cell culture chambers.

The culture medium reservoir is that reservoir where the initial culture medium in which the cells will be cultured is located, or it can also be a new culture medium, i.e., culture medium rich in nutrients and gases that is of interest for the purpose of replacing the culture medium in which the cells are contained in the cell culture process and is already considered deficient, and therefore disposable, culture medium. Advantageously, this culture medium reservoir allows providing fresh culture medium to the inside of the chambers when it is required in the culture process. Furthermore, this culture medium reservoir may be understood as a reservoir which can also house therein a recovery medium which can be introduced into the last cell culture chamber in which the cells have already reached their final size, i.e., the cell suspension culture process has already finalized, and are therefore extracted as an end product contained in a recovery medium.

The initial cell reservoir is that in which the cells object of being cultured in a culture medium are located. Advantageously, this initial cell reservoir allows introducing the cells to be cultured into any of the cell culture chambers. In particular, in a cell culture process which requires three cell culture chambers, for example, the cells are generally initially introduced into the chamber with the smallest internal volume, so that said cells subsequently and gradually expand to chambers with larger internal volumes in a consecutive manner. In another particular embodiment, if there is initially a large number of cells for a first cell culture chamber, these cells are distributed between the first two cell culture chambers so that they may be cultured in an optimal manner and an excess of cells per volume in which they are contained for culture is thereby prevented.

The residue reservoir is that reservoir for which residual fluids coming from any of the cell culture chambers are intended. For example, once the culture medium is considered deficient in nutrients and gases, and therefore disposable, it can be eliminated and collected in said residue reservoir. Advantageously, the fluid residue reservoir allows storing therein any residual fluid that is to be disposed of from inside any of the cell culture chambers. In other embodiments, the culture medium that has been disposed of due to a lack of nutrients and gases may be of interest for the user, for example, for recovering the metabolites or products of interest secreted by the cells during the culture. Nevertheless, the residue reservoir is a reservoir not only for storing disposable products, but also a reservoir where products of interest are stored.

The end product reservoir is that in which the end product, i.e., cells already cultured in a culture medium, is housed at the end of the cell culture process. This end product may be understood as the cultured cells contained in the culture medium or in a new medium that has been introduced in the last cell culture chamber, such as a recovery medium, for example. Advantageously, this end product reservoir allows quickly collecting the already cultured cells without having to intervene in the cell culture chambers.

When the measurement means detect that the culture medium which is circulating or contained inside the cell culture chamber is deficient in nutrients, such as glucose, for example, the measurement means are configured for sending a signal to the controller in order to actuate the fluid flow rate control means. The actuation of the control means provides the removal of the culture medium deficient in nutrients which is circulating and inside the cell culture chamber, such that this deficient culture medium is conducted to the residue reservoir. At the start of removing the culture medium deficient in nutrients, the fluid flow rate control means are operated so as to allow a new or fresh culture medium, stored in the culture medium reservoir, to be introduced into the cell culture chamber in which the cells are located to continue with cell culture.

In a particular embodiment, the network of channels comprises:

a first channel circuit suitable for conducting culture medium therein, and a second channel circuit suitable for conducting cells contained in a culture medium.

In particular, the measurement means are connected to the first channel circuit, and the fluid flow rate control means are connected in both circuits.

Advantageously, having two independent circuits provides a simpler channel design optimized for the present systems, as each circuit can be dedicated to different functions. In other words, the first circuit will handle the distribution and transport of culture medium throughout the system and its components. In turn, the second circuit will take care of the transport and distribution of the cell culture throughout the systems and their components. The risk of damage to or loss of cells due to the use of circuits with different functionalities is also advantageously reduced.

In a particular embodiment, the culture medium reservoir is connected to the first channel circuit, the initial cell reservoir is connected to the second channel circuit, the residue reservoir is connected to the first channel circuit, and the end product reservoir is connected to the second channel circuit.

In a particular embodiment, the fluid inlets-outlets of at least one of the cell culture chambers are connected to one another through the first channel circuit and/or through the second channel circuit.

In a particular embodiment, the system comprises a prechamber, preferably a cell transfection prechamber connected to a first cell culture chamber.

The cell transfection prechamber suitable for carrying out cell transfection required before the cell culture and expansion starts in the cell culture chambers. Said transfection prechamber is configured for controlling the cell transfection mechanism and conditions. In a particular embodiment, the cell transfection mechanisms can be electroporation, or gene transfection by means of viral vectors, among others.

Performing cell transfection before expanding the cells for culture advantageously allows said cells to be genetically modified to acquire certain conditions for subsequent use once they are cultured.

In a particular embodiment, the system comprises balancing means configured for balancing the cell culture chambers by means of actuating motors. In a particular embodiment, the motors are manually actuated by the user. In another particular embodiment, the motors are configured for being in data communication with the measurement means, such that according to the data monitored by these measurement means, the latter sends a signal to the controller in order to operate the motors when they consider that the cell culture chambers have to be balanced by the balancing means. The balancing means are connected to the controller the actuation of which can be predetermined and may vary according to the data obtained by the measurement means.

Advantageously, these balancing means allow the system to balance the cell culture chambers during the cell culture process, contributing to the suspension of the cells in the culture medium.

In a particular embodiment, the measurement means are connected to the network of channels and/or integrated inside the cell culture chambers.

In a particular embodiment, the measurement means comprise a biomass sensor; and/or an oxygen sensor, a pH sensor and/or a $CO_2$ sensor.

In a particular embodiment, the system is a suspension cell culture system suitable for housing inside the cell culture chambers cells suspended in culture medium.

In another particular embodiment, the system is a cell culture system by means of the adherence of cells to microparticles or surfaces. In the case of adherences to microparticles, in addition to preventing the cells from being extracted from inside the cell culture chambers before time, the retention means also prevent microparticles from being extracted by the culture medium current.

The present cell culture system advantageously allows carrying out the cell culture of cells in an optimal manner and under real time cell culture process tracking and monitoring. Therefore, the system provides thorough time control for the rate of development of the culture being performed in the system. Furthermore, as a result of the system configuration the secure and automatic expansion of the cells between cell culture chambers takes place, so the risk of contamination of the cell culture due to contact with external medium is advantageously reduced to zero since human intervention is prevented during the cell expansion process. Furthermore, the fact that the system is equipped to give the order to transfer cells to a chamber with a larger internal volume than the one in which they are initially located, and so on, progressively, and in turn to perform this cell culture transfer, prevents the cell culture from not being in optimal nutrients and oxygen conditions. Before the cell culture can even reach a non-optimal situation due to the fact that the volume in which the contained cells are located is too small to advance in their own culture, this cell culture is expanded to the inside of another chamber with a larger volume which covers the cells' needs for continued growth. The transfer or circulation of the cell culture in the system is operated by the control means comprised in the present system.

A second inventive aspect provides a method for culturing cells, characterized in that it is implemented in the cell culture system according to the first inventive aspect, and characterized in that it comprises the following steps:
  a) introducing cells contained in culture medium inside a first cell culture chamber,
  b) circulating the culture medium through the network of channels,
  c) transferring the cells contained in culture medium to the inside of a second cell culture chamber,
  d) repeating step b) inside the second cell culture chamber,
  e) obtaining the cultured cells;

wherein the method further comprises monitoring the state of the cell culture and/or cells through the measurement means in order to determine when the cells achieve certain properties and have to be transferred by means of step c) to a cell culture chamber with a larger internal volume than the one in which they are located, and so on, successively, were it necessary, to chambers of a larger internal volume.

The present cell culture method advantageously allows carrying out the cell culture of cells contained in culture medium in an optimal manner and in real time. This method is implemented in the defined system providing a thorough time control for rate of development of the culture being performed. Through this method, the safe and automatic expansion of the cells between cell culture chambers is achieved, so the risk of contamination of the cell culture due to contact with external medium is advantageously reduced to zero since it does not require human intervention during the cell expansion process. Before the cell culture can even be stressed due to the fact that the volume in which the cells contained in a first cell culture chamber are located is too small to advance in their own culture, this cell culture is expanded inside another chamber with a larger volume.

Advantageously, by monitoring the cell culture, the method can be completed automatically, without the need for there to be a user controlling the components of the system. In turn, this monitoring allows the user to be aware, in real time, of the state of the culture medium and/or cells.

In a particular embodiment, step d) of repeating step b) inside a second cell culture chamber can be repeated as many times as desired until having the target number of cultured cells.

In a particular embodiment, the method further comprises conditioning the culture medium through conditioning means if the measurement means determine that the culture medium is deficient, preferably deficient in gases and/or nutrients.

In a particular embodiment, the method comprises extracting the culture medium deficient in nutrients from inside the cell culture chamber and introducing new or fresh culture medium inside the cell culture chamber.

In a particular embodiment, the method further comprises balancing the cell culture chambers through balancing means.

All the features and/or steps of methods described in this specification (including the claims, description and drawings) can be combined in any combination, with the exception of combinations of mutually exclusive features.

DESCRIPTION OF DRAWINGS

These and other features and advantages of the invention will be more clearly understood based on the following detailed description of a preferred embodiment given only by way of illustrative and non-limiting example in reference to the attached drawings.

DETAILED DESCRIPTION OF THE INVENTION

Cell Culture System

Figure 1:
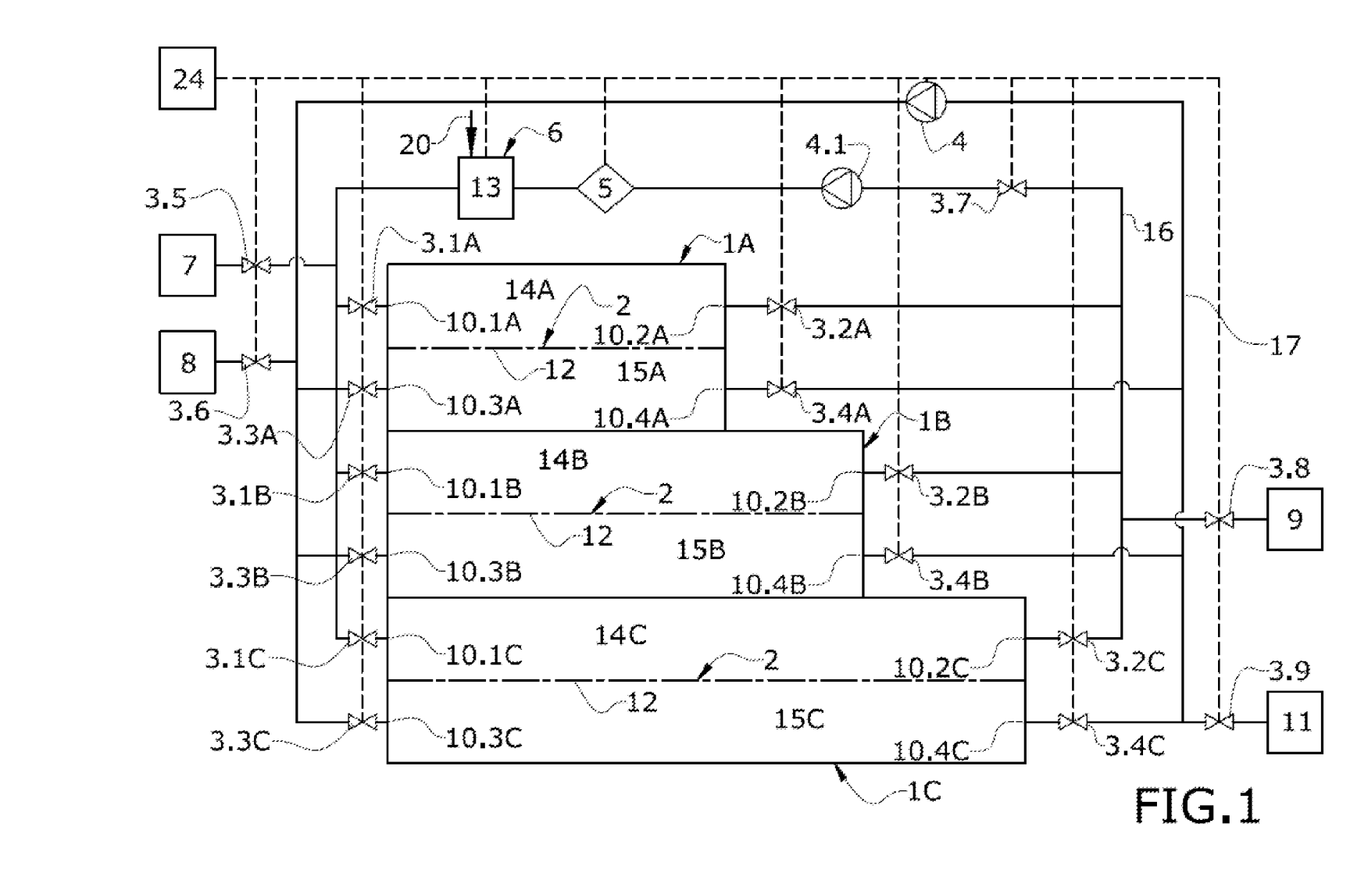
FIG. 1 schematically shows a cell culture system according to a particular embodiment of the first inventive aspect of the present invention.

FIG. 1 shows a particular example of a suspension cell culture system according to the first inventive aspect of the present invention. This system comprises three cell culture chambers (1: 1A, 1B, 1C) arranged such that they together form a stack. Each of these chambers (1A-1C) comprises an internal volume different from the others, and it can particularly be observed that said internal volume progressively increases from a first chamber (1A) to a second chamber (1B) and third chamber (1C).

Each of the cell culture chambers (1: 1A, 1B, 1C) shown in FIG. 1 comprises a plurality of fluid inlets-outlets (10.1A-10.4A, 10.1B-10.4B, 10.1C-10.4C) as well as filtration means (2) as cell retention means. Each chamber (1A-1C) further comprises a filter membrane (12) arranged going through the inside of the cell culture chamber (1A-1C) such that the internal space of this chamber (1A-1C) is split into a first compartment (14A-14C) and a second compartment (15A-15C), with the first compartment (14A-14C) being arranged above the second compartment (15A-15C) in the normal working position. The first compartment (14A-14C) comprises a first culture medium inlet (10.1A-10.1C) and a first culture medium outlet (10.2A-10.2C), both culture medium inlet (10.1A-10.1C) and outlet (10.2A-10.2C) connect to a network of channels that is common for the entire system. The second compartment (15A-15C) comprises a cell culture inlet (10.3A-10.3C) and a cell culture outlet (10.4A-10.4C), both cell culture inlet (10.3A-10.3C) and outlet (10.4A-10.4C) connect to a network of channels that is common for the entire system. The network of channels which is shown in the present system is formed by a first channel circuit (16) and by a second channel circuit (17), both channel circuits (16, 17) being connected to one another through the inside of each of the cell culture chambers (1). The first channel circuit (16) is suitable for conducting culture medium, whereas the second channel circuit (17) is suitable for conducting cells suspended in culture medium.

The system which is shown in FIG. 1 further comprises fluid flow rate control means (3: 3.1-3.9), in this particular example the flow rate control means (3: 3.1-3.9) are pinch valves. These pinch valves are in charge of regulating the passage of fluid through the network of channels, as well as allowing fluids to enter and/or exit the cell culture chamber (1A-1C).

The fluid flow rate control means comprises means (4) for driving the fluids through the network of channels. In this particular example, the means (4) for driving fluids are a peristaltic pump (4.1) which is in charge of extracting the fluid from inside each cell culture chamber (1A-1C) by means of pumping, as well as pumping said fluid for it to circulate throughout the network of channels in a constant manner, either between chambers or else inside of the same cell culture chamber (1A-1C). In particular, FIG. 1 shows a first pump (4.1) in charge of pumping the culture medium, and a second pump (4.2) in charge of pumping cells suspended in a medium.

The system shown in FIG. 1 further comprises a culture medium reservoir (7) suitable for housing therein initial or fresh culture medium. The culture medium reservoir (7) is connected to the network of channels to provide fresh or new culture medium inside any of the cell culture chambers (1A-1C) when needed.

The system further comprises an initial cell reservoir (8) suitable for housing therein initial cells object of being cultured in suspension inside the cell culture chambers (1A-1C). This initial cell reservoir (8) is connected to the network of channels to provide cells already contained in an initial liquid medium to the inside of the cell culture chamber (1A-1C).

FIG. 1 furthermore shows a residue reservoir (9) suitable for housing therein residual fluids coming from any of the cell culture chambers (1A-1C). This residue reservoir (9) is connected to the network of channels so that during the suspension cell culture process, the culture medium deficient in nutrients and gases determined to be disposable by the fungible is conducted into the residue reservoir (9).

FIG. 1 also shows an end product reservoir (11) connected to the network of channels. This end product reservoir (11) is a vessel housing the already cultured cells coming from any of the cell culture chambers (1A-1C) after the suspension cell culture process.

FIG. 1 furthermore shows a controller (24) in connection with the fluid flow rate control means (3: 3.1-3.9), with the conditioning means (6), measurement means (5), and the peristaltic pumps (4.1, 4.2).

The system of FIG. 1 further comprises measurement means (5), which in one embodiment are a sensor connected to the network of channels. These measurement means (5) are in charge of measuring and monitoring the state of the culture medium and/or cells to thereby enable knowing the state of the cell culture, i.e., the state of the cells in the different suspension cell culture phases. In a particular embodiment, the measurement means (5) are glucose and lactate sensors connected to the network of channels, in particular, in FIG. 1 they are connected to the first circuit (16) of the network of channels. The measurement means (5) are in connection with the controller (24) such that all the data measured and monitored by said measurement means (5) is sent to the controller (24) so that the latter can take it into account in order to operate the fluid flow rate control means (3: 3.1-3.9) and culture medium conditioning means (6).

The system comprises culture medium conditioning means (6) connected to the network of channels. When the controller (24) determines, through the data measured by the measurement means (5), that the culture medium is no longer fresh, i.e., it is deficient in gases for the cell culture, this culture medium is conditioned through the conditioning means (6), thereby providing again to the culture medium those gases required to continue with the cell culture of cells suspended inside the cell culture chamber (1A-1C). The conditioning means (6) comprise a conditioning chamber (13) in which culture medium deficient in gases can be introduced in order to be conditioned and to thereby recover the gases required for the cell culture. In order to add the culture medium deficient in gases that is deposited in the conditioning chamber (13), the system comprises gas injection means (20).

On the other hand, when the controller (24) determines that the culture medium is no longer fresh, i.e., it is deficient in nutrients, this culture medium is discarded and conducted to the residue reservoir (11) through the operation of the fluid flow rate control means (3: 3.1-3.9). In turn, a new fresh culture medium is introduced in the cell culture chamber (1) in which the cells are located to enable continuing with growth.

Figure 2:
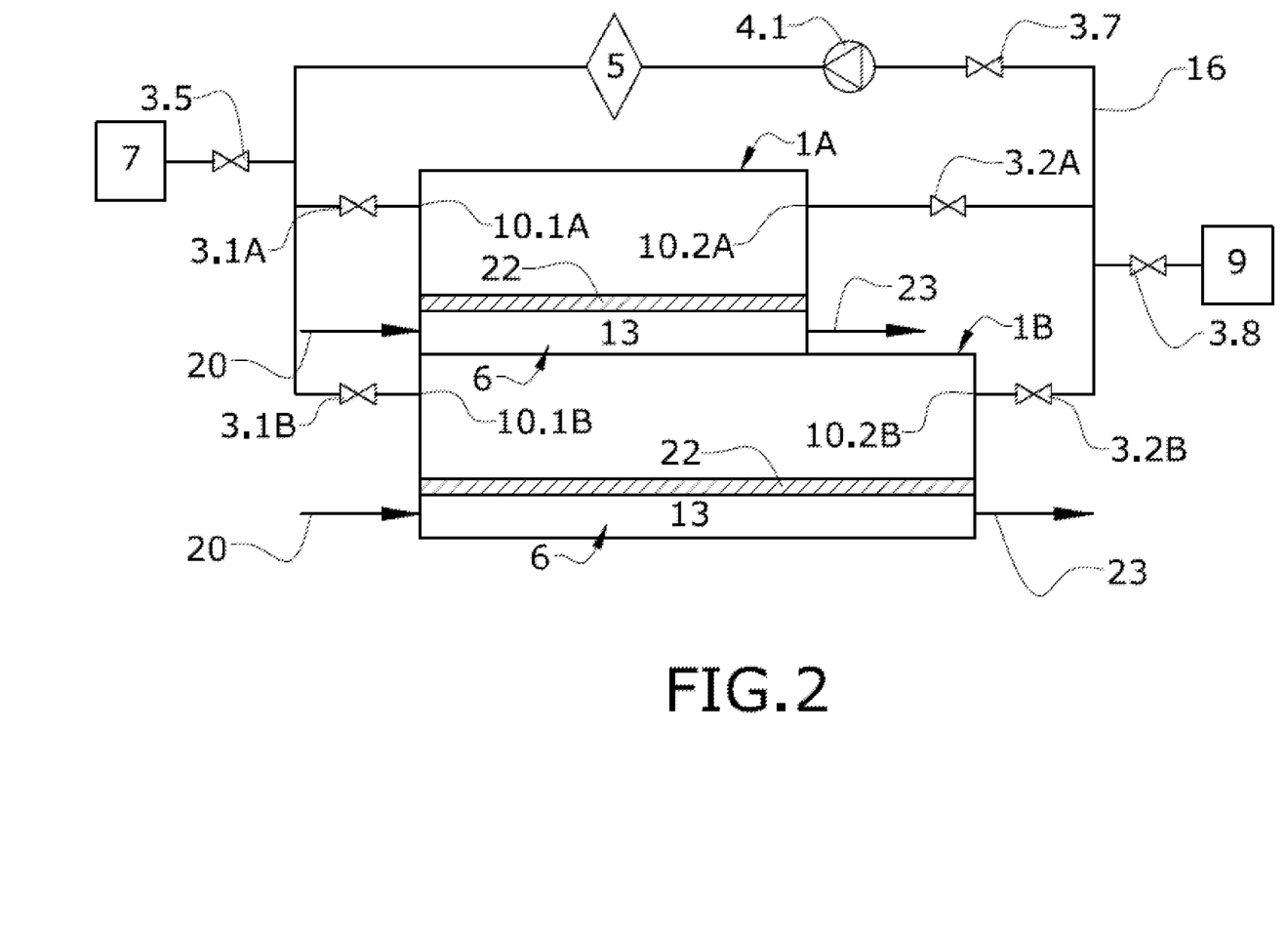
FIG. 2 schematically shows a cell culture system showing a first channel circuit according to a particular embodiment of the first inventive aspect of the present invention.

FIG. 2 shows a particular example of a cell culture system according to the first inventive aspect of the present invention. This system comprises two cell culture chambers (1A-1B) stacked one on top of the other, such that the first chamber (1A) arranged in the upper part of said stack has a smaller internal volume than the second cell culture chamber (1B) below same. Each of the cell culture chambers (1A-1B) comprises respectively a culture medium inlet (10.1A-10.1B) and culture medium outlet (10.2A-10.2B).

In the system of FIG. 2, the conditioning means (6) comprise two conditioning chambers (13), one for each cell culture chamber (1A-1B). Each conditioning chamber (13) is in contact with the inside of each cell culture chamber (1A-1B) respectively through a gas-permeable membrane (22). The conditioning means (6) further comprise gas injection means (20) configured for injecting gases into the conditioning chamber (13), as well as a gas outlet or expulsion means (23) configured for releasing the gas that is in the conditioning chamber (13). In particular, said FIG. 2 only shows the first channel circuit (16) and the connections thereof with the different elements making up the systems. The first culture medium inlet (10.1A) and first culture medium outlet (10.2A) of the first cell culture chamber (1A) are both connected to one another and to the other cell culture chamber (1B) through the first channel circuit (16). A plurality of fluid flow rate control means (3: 3.1-3.9), means (4) for driving fluids, and measurement means (5) are also connected to this first channel circuit (16). FIG. 2 furthermore shows a culture medium reservoir (7) connected to the first channel circuit (16) of the network of channels of the system, as well as a residue reservoir (9) also connected to said first channel circuit (16). The extraction of culture medium from the inside of the chambers (1A-1C) through the first culture medium outlet (10.2A-10.2B) and the subsequent circulation thereof through this first channel circuit (16) is driven by a first pump (4.1) and regulated by the fluid flow rate control means (3: 3.1-3.9). In turn, the introduction of culture medium inside the chambers (1A-1C) through the first culture medium inlet (10.1A-10.1B) is also regulated by the fluid flow rate control means (3: 3.1-3.9).

This system further comprises a controller (not shown) in connection with the fluid flow rate control means (3: 3.1-3.9) with the conditioning means (6), and in data communication with the measurement means (5). The conditioning of the culture medium contained and circulating inside a cell culture chamber (1A-1B) is performed through the interaction of the gas rich in nutrients injected into the conditioning chamber (13) with the culture medium through the membrane (22) permeable.

The system also comprises a first pump (4.1) (means for driving fluids) connected to the first channel circuit (16) and configured for circulating culture medium through the chambers (1A-1B) at a pre-determined speed and with a particular flow direction (not shown).

Figure 3:
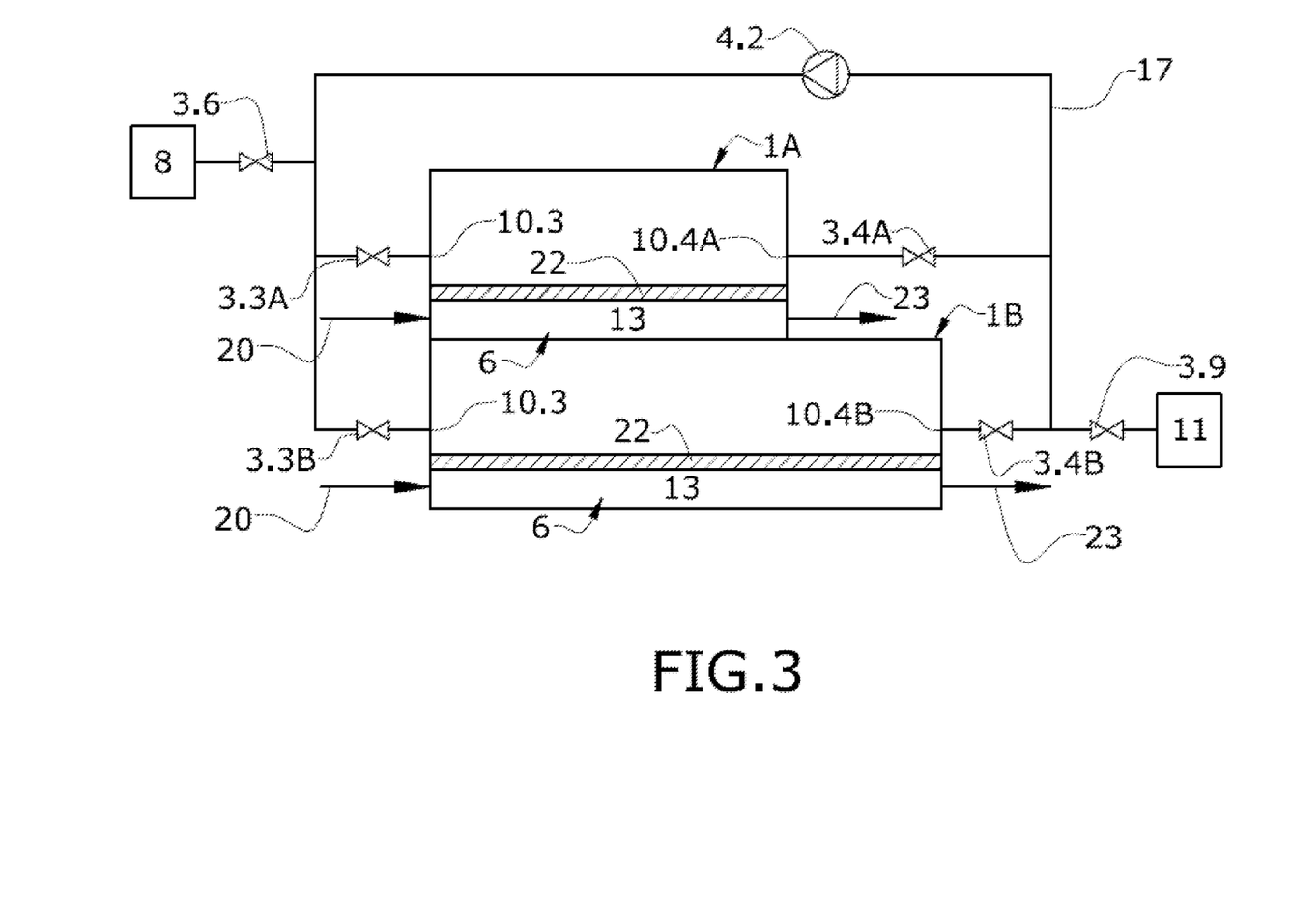
FIG. 3 schematically shows a cell culture system showing a second channel circuit according to a particular embodiment of the first inventive aspect of the present invention.

FIG. 3 shows a particular example of a cell culture system according to the system of FIG. 2. This system comprises two cell culture chambers (1A-1B) stacked one on top of the other as in FIG. 2. Each of the cell culture chambers (1A-1B) comprises a second cell culture inlet (10.3A-10.3B) and second cell culture outlet (10.4A-10.4B). This system further comprises conditioning means (6) like the ones that are shown in the system of FIG. 2. In particular, said FIG. 3 only shows the second channel circuit (17) and the connections thereof with the different elements making up the system. The second cell culture inlet (10.3A-10.3B) and second cell culture outlet (10.4A-10.4B) of the chambers (1A-1B) are connected to one another through the second channel circuit (17). Also connected to this second channel circuit (17) there is a plurality of fluid flow rate control means (3: 3.1-3.9) and means for driving fluids, particularly a second pump (4.2) like the first pump (4.1) described in FIG. 2. FIG. 3 furthermore shows an initial cell reservoir (8) connected to the second channel circuit (17) of the network of channels of the system, as well as an end product reservoir (11) also connected to said second channel circuit (17). The extraction of cell culture from inside the cell culture chamber through the second cell culture outlet (10.4A-10.4B) and the subsequent circulation thereof through this second channel circuit (17) is driven by the second pump (4.2) and regulated by the fluid flow rate control means (3: 3.1-3.9). In turn, the introduction of cell culture inside any of the cell culture chambers (1A-1B) through the second cell culture inlet (10.3A-10.3B) is also regulated by the fluid flow rate control means (3: 3.1-3.9).

The first channel circuit (16) which is shown in FIG. 2 is suitable for circulating therein culture medium or recovery medium; whereas the second channel circuit (17) which is shown in FIG. 3 is suitable for circulating therein cell culture, i.e., cells suspended in culture medium or recovery medium.

Figures 4, 5, 6:
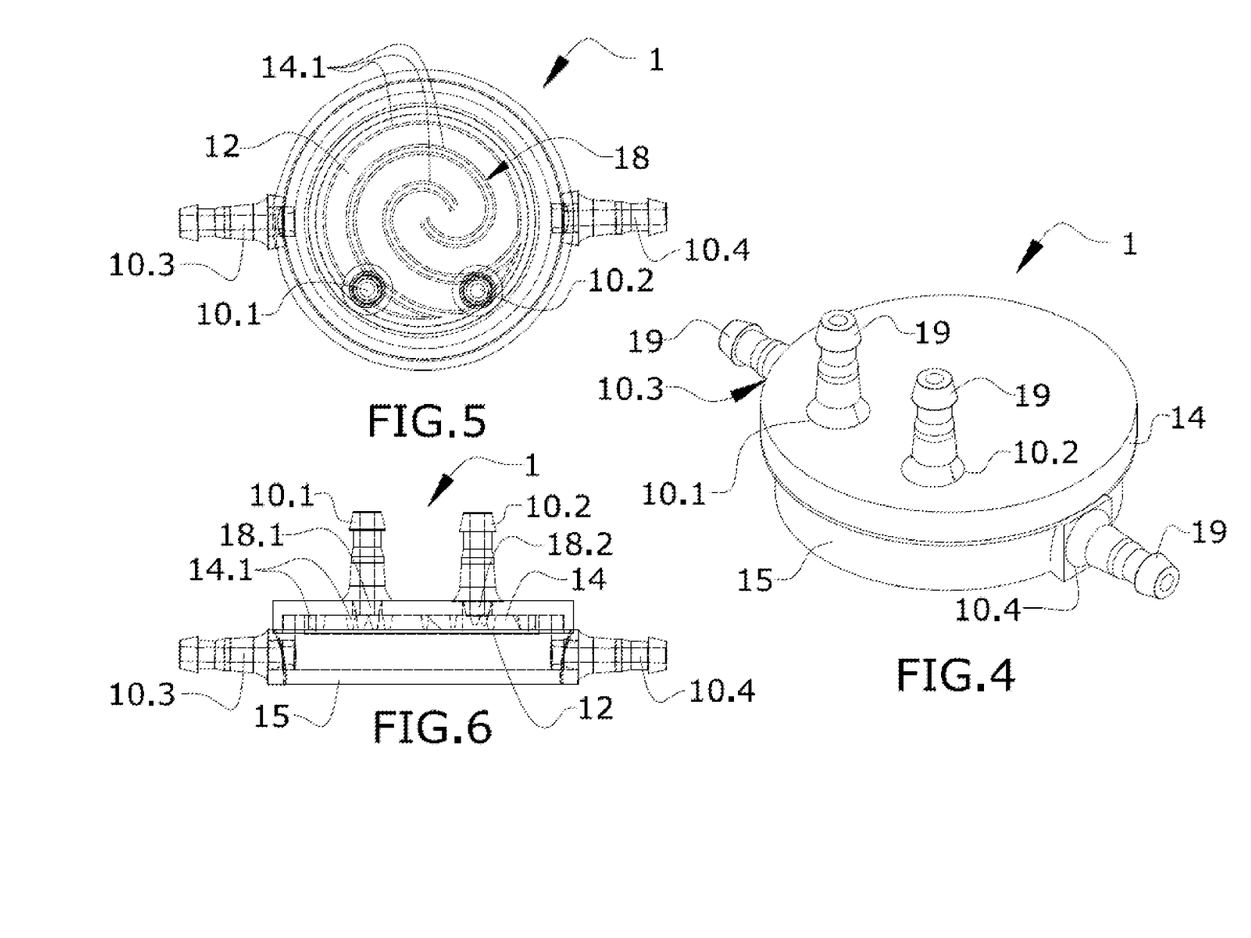
FIG. 4 shows a schematic perspective view of a cell culture chamber according to a particular embodiment of the first inventive aspect of the present invention.
FIG. 5 shows a schematic top view of the cell culture chamber which is shown in FIG. 4.
FIG. 6 shows a schematic sectioned side view of the cell culture chamber which is shown in FIG. 4.

FIG. 4 shows a perspective view of a particular example of a cell culture chamber (1). This cell culture chamber (1) comprises two internal compartments, a first compartment (14) arranged above a second compartment (15). The cell culture chamber (1) further comprises a plurality of connectors (19) coupled to each inlet-outlet (10.1-10.4) comprised in said chamber (1). These connectors (19) are in charge of connecting each inlet-outlet (10.1-10.4) with the channels/tubes of the network of channels (not shown in the drawing).

In particular, the cell culture chamber (1) of FIG. 4 shows a first culture medium inlet (10.1) and a first culture medium outlet (10.2), with both inlet (10.1) and outlet (10.2) being connected to a connector (19), respectively, and arranged in the upper part of the first compartment (14) of the cell culture chamber (1).

Furthermore, the cell culture chamber (1) shows a second cell culture or initial cell inlet (10.3) and a second cell culture outlet (10.4), with both inlet (10.3) and outlet (10.4) being connected to a connector (19), respectively, and arranged in the lateral part of the second compartment (15) of said cell culture chamber (1). Both compartments (14, 15) are separated from one another by a filter membrane (shown in FIG. 6) which allows there to be fluid communication inside the cell culture chamber (1) between both compartments (14, 15).

FIG. 5 shows a top view of the inside of the cell culture chamber (1) which is shown in FIG. 4, where the internal structuring of the first compartment (14) as well as the first culture medium inlet (10.1) and the first culture medium outlet (10.2) are particularly shown with a discontinuous line. In this particular example, the first compartment (14) comprises a plurality of walls (14.1) arranged in circular spiral form defining a culture medium distribution channel (18). This culture medium distribution channel (18) is connected along its entire extension with the filter membrane (12), as shown in FIG. 6. Furthermore, the distribution channel (18) comprises a first end (18.1) connected with a first culture medium inlet (10.1), and a second end (18.2) connected with a first culture medium outlet (10.2).

Therefore, as the culture medium enters the first compartment (14) through the culture medium inlet (10.1), this culture medium runs along the distribution channel (18) such that it sweeps the entire surface of the filter membrane (12) until it reaches the first culture medium outlet (10.2) and is extracted through said first outlet (10.2).

FIG. 6 shows a sectioned side view of the cell culture chamber (1) which is shown in FIGS. 5 and 6. FIG. 6 shows in detail the difference in volume between compartments (14, 15).

The first compartment (14) has an internal volume smaller than the internal volume of the second compartment (15).

Figure 7:
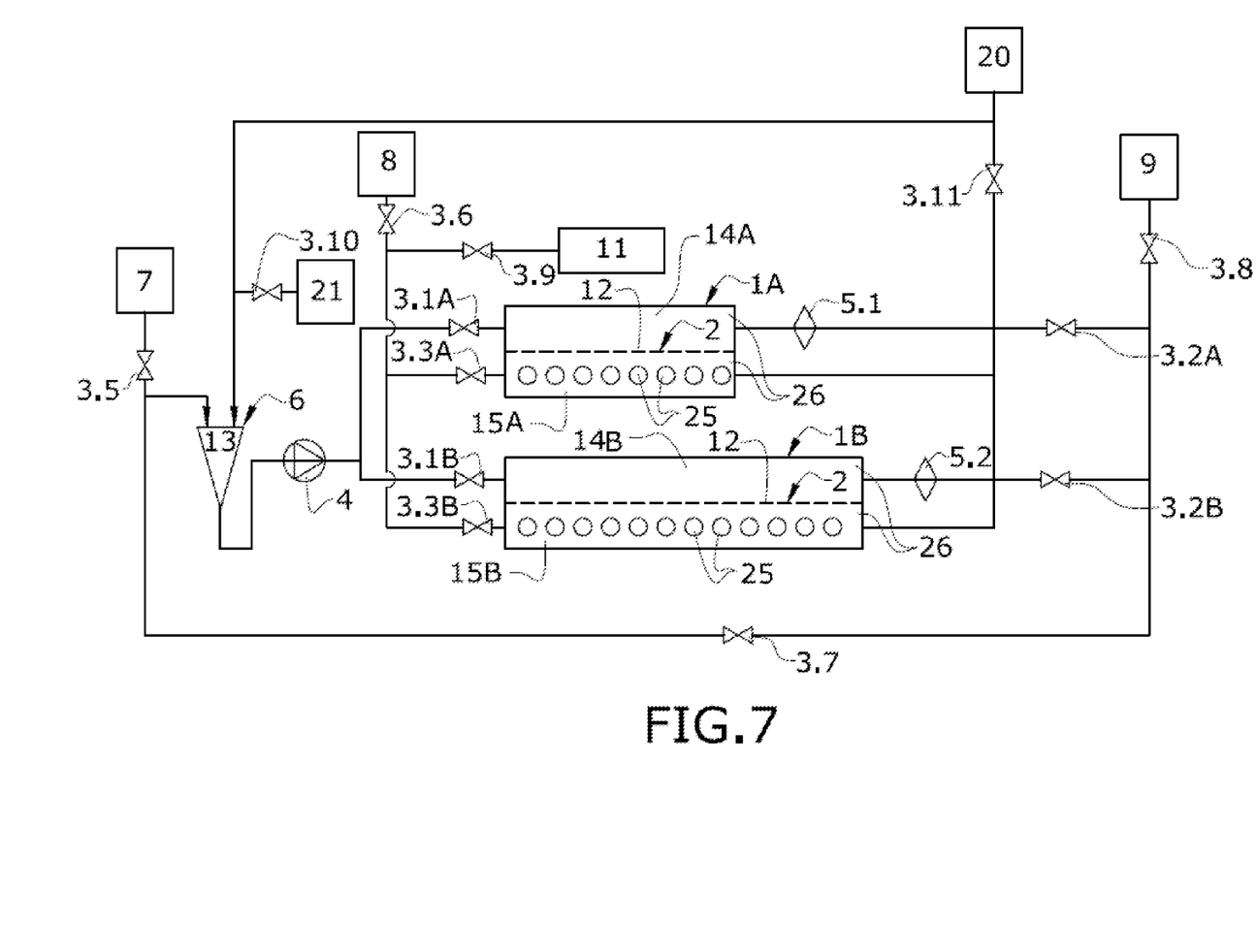
FIG. 7 shows a cell culture system according to a particular embodiment of the first inventive aspect of the present invention.

FIG. 7 shows a particular example of a system, according to the first inventive aspect, comprising two cell culture chambers (1: 1A, 1B), the first chamber (1A) having an internal volume smaller than the internal volume of the second chamber (1B). Each of the chambers (1A-1B) comprises a filter membrane (12) as retention means, arranged going through the inside of the cell culture chamber (1) such that the internal space of this chamber (1A-1B) is split into a first compartment (14A-14B) and a second compartment (15A-15B), with the first compartment (14A-14B) arranged above the second compartment (15A-15B) in the normal working position. Both cell culture chambers (1A-1B) connect to one another through a network of channels. Circulating culture medium (26) would be found in the first compartment (14A-14B), whereas the cells (25) contained in culture medium (26) which is filtered between both compartments are located in the second compartment (15A-15B).

The system which is shown in FIG. 7 further comprises a plurality of valves (3: 3.1-3.10) connected to the network of channels. The system further comprises a pump (4) also connected to the network of channels.

The system which is shown in FIG. 7 comprises a culture medium reservoir (7), an initial cell reservoir (8), a residue reservoir (9), and an end product reservoir (11), all of which reservoirs being like the ones shown in FIG. 1.

The system of FIG. 7 further comprises a first sensor (5.1) and a second sensor (5.2), both being connected to the network of channels and each configured for monitoring the state of the culture medium circulating through the first cell culture chamber (1A) and second cell culture chamber (1B), respectively.

The first sensor (5.1) and second sensor (5.2) of the system shown in FIG. 7 each comprises gas and nutrient sensors, i.e., they are sensors configured for measuring the pH and the level of $O_2$ contained in the culture medium and the level of glucose and lactate, respectively. The sensors (5.1, 5.2) are in connection with the controller (not shown in the drawing) such that all the data measured and monitored by said sensors (5.1, 5.2) is sent to the controller in order to operate the fluid flow rate control means (3: 3.1-3.10) and culture medium conditioning means (6) depending on the needs of the cell culture.

In the system shown in FIG. 7, the conditioning means (6) for the culture medium comprise a conditioning chamber (13) in which culture medium deficient in gases can be introduced to be conditioned and to thereby recover the gases required for the cell culture, or said chamber can also be to deposit the new fresh culture medium before being pumped towards the cell culture chambers (1A-1B). To condition the culture medium deficient in gases deposited in the conditioning chamber (13), the system comprises gas injection means (20). Furthermore, the system comprises gas release means (21) in the event of excess pressure in the suspension cell culture process. These gas injection means (20) as well as the gas release means (21) are also in connection with the controller (not shown), such that they can be operated when determined by said controller.

Figure 8:
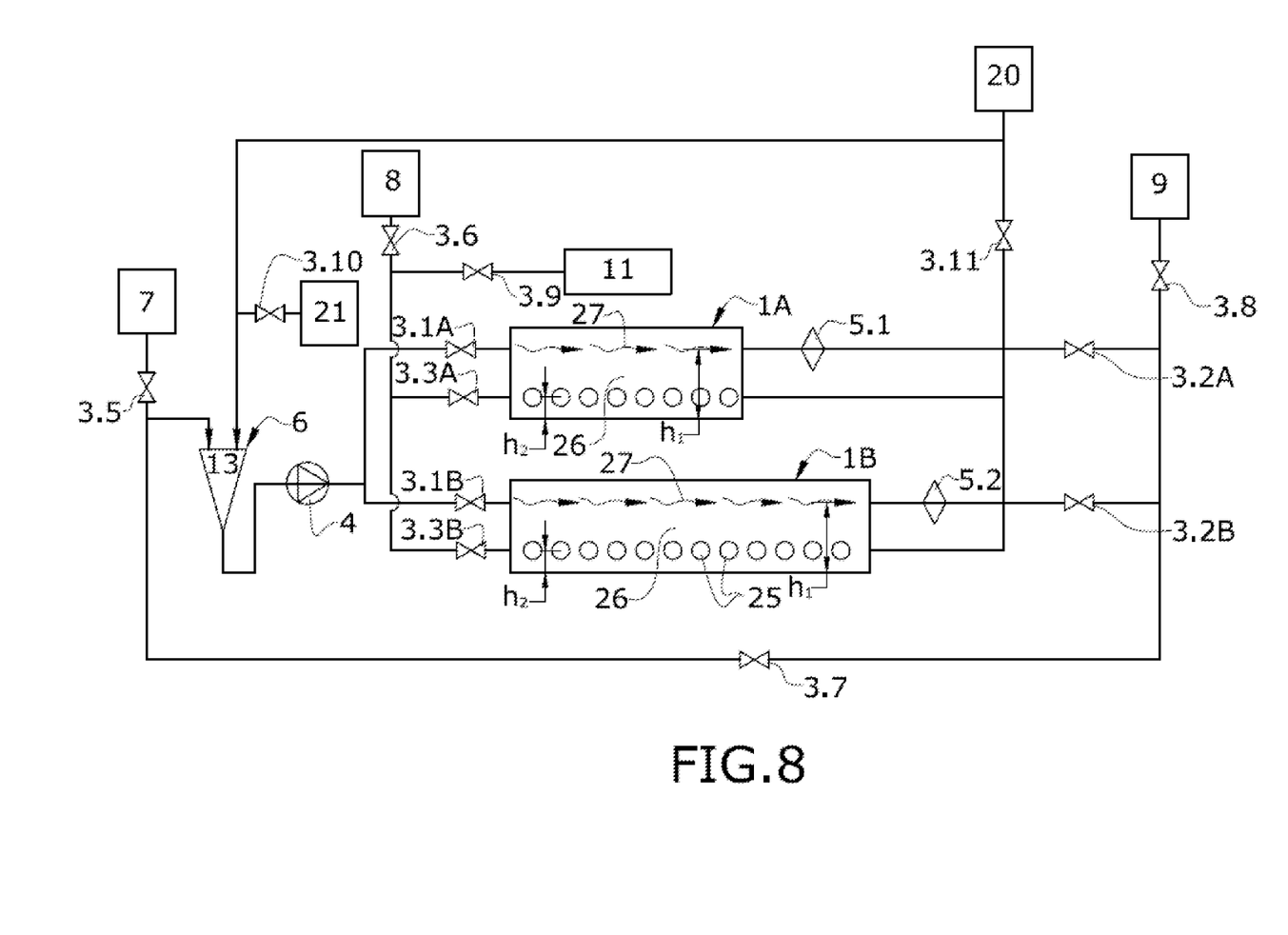
FIG. 8 shows a cell culture system according to a particular embodiment of the first inventive aspect of the present invention.

FIG. 8 shows a particular example of a system comprising two cell culture chambers (1A, 1B), with the first chamber (1A) having a smaller internal volume than that of the second chamber (1B). Both cell culture chambers (1A-1B) connect to one another through a network of channels. This system comprises a peristaltic pump (4) connected to the network of channels and in charge of driving culture medium (26) to the inside of the cell culture chambers (1A-1B). The culture medium (26) is driven by said pump (4) at a pre-determined speed and with a flow direction at a first height (h1) with respect to the base of the chamber (1A-1B), this first height being greater than a second height (h2) at which the cells (25) contained inside the chamber (1A-1B) are arranged with respect to the base of the chamber (1A-1B). Therefore, when the culture medium is circulated through the inside of the chamber (1A-1B) cells (25) are prevented from being entrained out of this chamber (1A-1B) sooner than required.

In a particular example, the flow direction of the culture medium circulating through the inside of the chambers (1A-1C) is essentially parallel to the arrangement of the cells (25) contained in said chambers.

The system which is shown in FIG. 8 further comprises a plurality of valves (3: 3.1-3.10) connected to the network of channels.

The system which is shown in FIG. 8 in turn comprises a culture medium reservoir (7), an initial cell reservoir (8), a residue reservoir (9), and an end product reservoir (11), all of which reservoirs being like the ones shown in FIG. 1.

The system of FIG. 8 further comprises a first sensor (5.1) and a second sensor (5.2), both being connected to the network of channels and each configured for monitoring the state of the culture medium circulating through the first cell culture chamber (1A) and second cell culture chamber (1B), respectively. These sensors (5.1, 5.2) which are shown in FIG. 8 are identical to those described for FIG. 7.

Furthermore, the system which is shown in FIG. 8 comprises conditioning means (6) for the culture medium (26), which means are like those described for FIG. 7.

It can be seen in FIG. 8 how the flow direction (27) of the culture medium (26) circulating through the inside of the chambers (1A, 1B) is located at a first height (h1) with respect to the base of the cell culture chambers (1A, 1B), and the arrangement of the cells (25) contained in culture medium (26) are located at a second height (h2) with respect to the base of the cell culture chambers (1A, 1B). The first height (h1) is greater than the second height (h2).

Cell Culture Method

The steps of the cell culture method according to the present invention are described below, with this method being implemented in the system which is shown in FIG. 7, and which corresponds with the system of the first inventive aspect. In particular, it is a suspension cell culture method. The method comprises the following steps according to the present invention:

a) introducing cells (25) suspended in culture medium (26) inside the first cell culture chamber (1A), b) circulating the culture medium (26) through the network of channels, c) transferring the cells (25) suspended in culture medium (26) to the inside of a second cell culture chamber (1B), d) repeating step b) inside the second cell culture chamber (1B), e) obtaining the cultured cells (25);

wherein the method further comprises monitoring the state of the cell culture and/or cells (25) through the measurement means (5) in order to determine when the cells (25) achieve certain properties and have to be transferred by means of step c) to a cell culture chamber (1B) with a larger internal volume than the one in which they are located.

Before starting the suspension cell culture method, the initial functional state of the system is with all the valves (3: 3.1, 3.2, 3.3, 3.4, 3.5, 3.6, 3.7, 3.8, 3.9, 3.10, 3.11, 3.12, 3.11) closed and the pump (4) deactivated.

Before step a), the conditioning chamber (13) is filled with culture medium (26) coming from the culture medium reservoir (7). This filling is carried out by means of the opening of valve (3.5) and valve (3.10), which allows releasing pressure from the network of channels and circulating the culture medium (26) into said conditioning chamber (13).

The functional scheme of the system in step a) is the following:
pump (4) operated,
valve (3.1A) open,
valve (3.6) open, and
valve (3.3A) open.

Once the cells (25) are suspended in the culture medium (26) inside the first chamber (1A), the culture medium circulates between both compartments (14, 15) of the chamber through the filter membrane (12). Cell culture is introduced inside the first chamber (1A) until the culture medium reaches the first sensor (5.1). In a particular example according to the cell culture system which is shown in FIGS. 2 and 3, the cells are introduced inside the first chamber (1A) through the inlet (10.3) together with the culture medium which is introduced through the inlet (10.1).

In a particular example, before step b) the cell culture chambers (1A-1B) are balanced by means of the action of motors comprised in the system (not shown in the drawings). The functional scheme of the system during balancing is with all the valves (3: 3.1, 3.2, 3.3, 3.4, 3.5, 3.6, 3.7, 3.8, 3.9, 3.10, 3.11, 3.12, 3.11) closed and the pump (4) deactivated. In a particular embodiment, the motors provide a balancing of the cell culture chambers (1A-1B) of −10 to 10 degrees.

The functional scheme of the system in step b) is the following:
valve (3.1A) open,
valve (3.2A) open,
valve (3.7) open, and
pump (4) operated.

In a particular embodiment, the culture medium (26) circulates through the network of channels in the circulation step, entering and exiting the first cell culture chamber (1A) for about 30 seconds.

In step b), in addition to circulating the culture medium (26) itself that had been introduced into the chamber, the culture medium (26) contained in the conditioning chamber (13) is also circulated, such that it is combined with the other one. It may be necessary to introduce a larger amount of culture medium (26) for circulation, and to that end fresh culture medium (26) coming from the fresh culture medium reservoir (7) inside the conditioning chamber (13) is introduced again, as was explained above.

In a particular example according to the cell culture system which is shown in FIGS. 2 and 3, once the cells are introduced inside the first chamber (1A) the culture medium circulates, entering through the inlet (10.1) and exiting through the outlet (10.2) of said cell culture chamber at a pre-determined speed such that it prevents the cells suspended in the chamber (1A) from being entrained by the culture medium flow through the outlet (10.2).

During step b), if the data measured by the first sensor (5.1) and received by the controller (not shown in FIG. 7) determines that the culture medium (26) is deficient in gases, the controller sends a signal to the operating means (6) in order to allow the storage of the culture medium (26) that is circulating in the conditioning chamber (13), and gas injection means (20) are operated by means of opening valve (3.11). Gases are thereby incorporated into the culture medium (26) to condition it, and this culture medium (26) is again conducted to the inside of the chamber (1A-1B) in order to advance with the culture of the cells.

During step b), if the first sensor (5.1) determines that the culture medium (26) is deficient in nutrients, this first sensor (5.1) outputs a signal to the controller in order to operate some valves so as to allow the culture medium (26) deficient in nutrients to be discarded, i.e., it is conducted to the residue reservoir (9). In this disposal phase of culture medium deficient in nutrients, the functional scheme of the system is the following:
valve (3.2A) open,
valve (3.8) open, and
valve (3.7) closed.

When the culture medium deficient in nutrients is discarded, the system provides new culture medium to the inside of the culture chamber (1A-1B) as explained above in order for the cell culture process to continue. Once the new culture medium (26) has been introduced into the first cell culture chamber (1A) and through the network of channels, this culture medium is circulated until the first sensor (5.1) measures whether the culture medium is deficient in gases or nutrients, or if the cells must be transferred to a second cell culture chamber (1B). If the controller determines that the culture medium is deficient in gases or nutrients, through the data measured by the first sensor (5.1), before the cells (25) have to be transferred to a new chamber, the system reacts as explained above for each of these situations, either conditioning the culture medium (26) circulating through the system or discarding this culture medium (26) and introducing a new one.

During step b), if the first sensor (5.1) measures that the cells (25) need to expand into a larger volume, the controller operates the system so as to proceed with step c) of transferring cells (25) suspended in culture medium (26) to a second cell culture chamber (1B).

In step c) the functional scheme of the system is the following:
valve (3.1A) open,
valve (3.3A) open,
valve (3.3B) open, and
pump (4) operated.

In a particular embodiment, in step c) of transferring cells between cell culture chambers (1A-1B), the balancing motors are activated (with all the valves being closed), and these motors balance the cell culture chambers (1A-1B) from −10 to 10 degrees. In a particular example, after balancing the balancing motors stop, leaving the cell culture chamber (1A-1B) in question balanced at −20 degrees with respect to the initial position of the system in order to allow the cells (25) suspended in culture medium (26) to go into the second cell culture chamber (1B).

Once the cells (25) are transferred to a second cell culture chamber (1B), the culture process continues as explained for the first cell culture chamber (1A) as it is defined in step d) for circulating the culture medium. During step d), a second sensor (5.2) will be monitoring the state of the culture medium and with the data that is measured it is sent to the controller, such that the controller determines the state of the cells (25). Nevertheless, if the controller determines that the culture medium (26) is deficient in gases or nutrients, the controller would operate the system appropriately as explained for the first cell culture chamber (1A).

If the second sensor (5.2) measures that the system has already reached its end product, i.e., the cells (25) have already been cultured, these cells (25) are collected in step e) of the present method.

In step e), the functional scheme of the system is the following:
- valve (3.3B) open,
- valve (3.9) open,
- valve (3.11) open, and
- pump (4) disconnected.

For circulating the cultured cells suspended in a culture medium to the end product reservoir (11), air is injected into the network of channels which helps said circulation. This injection of air is carried out by gas injection means (20), such that when the valve (3.11) is opened, the air is injected into the second compartment (15) of the second cell culture chamber (1B) for circulating said end product.

In a particular embodiment, in step e) for obtaining the end product, the balancing motors are activated (with all the valves being closed), and these motors balance the second cell culture chamber (1B) from −10 to 10 degrees. In a particular example of step e), after balancing the balancing motors stop, keeping the second cell culture chamber (1B) in question balanced at −20 degrees with respect to the initial position of the system to thereby allow the end product to be circulated completely to the end product reservoir (11). Once the end product has been collected, the balancing motors position the cell culture chambers (1) in the initial position of the system.

In a particular embodiment, the measurement means (5) comprise a third sensor (not shown in the drawings) connected to the network of channels and being in data communication with the controller. This third sensor is configured for detecting when only air is circulating through the network of channels, which means that the entire end product has already been collected inside the end product reservoir (9). The third sensor is located before the end product reservoir (11).

For a suspension cell culture method implemented in the system which is shown in FIG. 8, the same steps described for the method implemented by the system of FIG. 7 would be reproduced. However, in this case, in step b) the culture medium (26) that is circulated is driven into the chamber (1A-1B) by means of the pump (4) at a pre-determined speed and with a flow direction (27) at a first height (h1) with respect to a base of the chamber (1A-1B), this first height being greater than a second height (h2) at which the cells (25) contained in culture medium (26) are located, such that these cells (25) contained in said chambers are prevented from being entrained out of the cell culture chamber (1A-1B) sooner than required. In other words, as an alternative to the solution proposed for the system of FIG. 7, in which a filtration membrane is combined with the particularities of the system itself, the system which is shown in FIG. 8 proposes including the culture medium at a speed and with a predetermined flow direction according to the features of the system itself, as well as the cell culture. Therefore, in contrast, that which has been described above concerning the suspension culture method implemented by the system which is shown in FIG. 7 would also apply for the suspension culture method implemented by the system of FIG. 8.

The invention claimed is:

1. A cell culture system, characterized in that it comprises:
   a plurality of cell culture chambers configured for culturing therein cells contained in a culture medium, and configured for being in fluid communication with one another through a network of channels,
   fluid flow rate control means for a fluid circulating through the network of channels,
   culture medium conditioning means configured for providing to deficient culture medium gases and/or nutrients which have been lost,
   measurement means configured for monitoring the state of the culture medium and/or cells,
   a controller in connection with the fluid flow rate control means and/or with the conditioning means, the controller being configured for being in data communication with the measurement means,
wherein:
   each cell culture chamber comprises a plurality of fluid inlets-outlets;
   the plurality of cell culture chambers all comprise different internal volumes; and
   the plurality of cell culture chambers are arranged sequentially so that the internal volume of which increases according to culture process needs;
   the controller, according to the data measured by the measurement means, is furthermore configured for:
   operating the conditioning means, and/or
   operating the fluid flow rate control means such that all the cells contained in culture medium inside a first chamber are transferred to the inside of a second chamber the internal volume of which is larger than the internal volume of the first chamber, and so on, successively, were it necessary, to chambers with a larger internal volume until the cell culture process ends; and
   wherein the system further comprises a cell retention means configured for retaining cells inside the cell culture chambers until the controller operates the flow rate control means which allow all the cells to be transferred to another cell culture chamber with a larger internal volume than the cell culture chamber in which they are located or to be extracted as end product or cultured cells or to be transferred to another process.

2. The system according to claim 1, characterized in that the cell retention means comprise filtration means arranged inside the cell culture chambers and being configured for filtering the culture medium and retaining the cells inside each cell culture chamber.

3. The system according to claim 2, characterized in that the filtration means of at least one of the cell culture chambers comprises a filter membrane splitting said cell culture chamber into:
   a first compartment suitable for containing therein a culture medium, and
   a second compartment suitable for containing therein cells contained in a culture medium,
   wherein the filter membrane is configured for allowing the passage of the culture medium between both compartments and for retaining the cells in the second compartment.

4. The system according to claim 1, characterized in that the filtration means of at least one of the cell culture chambers comprises at least one filter arranged in at least one of the fluid inlets-outlets of the cell culture chamber.

5. The cell culture system according to claim 1, characterized in that the cell retention means comprise a pump configured for circulating culture medium through the chamber at a pre-determined speed and with a flow direction at a first height (h1) with respect to a base of the chamber, this first height being greater than a second height (h2) at which the cells contained inside the chamber are arranged with respect to the base of the chamber, such that when the culture medium is circulated through the inside of the chamber, the cells are prevented from being entrained out of this chamber sooner than required.

6. The system according to claim 1, characterized in that the conditioning means comprise a conditioning chamber configured for containing gases therein, the conditioning chamber being connected to the cell culture chambers through a gas-permeable membrane.

7. The system according to claim 1, characterized in that the culture medium conditioning means comprise:
a conditioning chamber connected to the network of channels and configured for housing culture medium therein, and
means for injecting at least one gas into the conditioning chamber.

8. The system according to claim 1, characterized in that it comprises:
a culture medium reservoir connected to the network of channels and configured for being in fluid communication with the inside of the cell culture chambers, and/or
an initial cell reservoir connected to the network of channels and configured for being in fluid communication with the inside of the cell culture chambers, and/or
a residue reservoir connected to the network of channels and configured for housing therein residual fluids coming from the inside of the cell culture chambers, and/or
an end product reservoir connected to the network of channels and configured for being in fluid communication with the inside of the cell culture chambers.

9. The system according to claim 1, characterized in that it comprises a prechamber, preferably a cell transfection prechamber connected to a first cell culture chamber.

10. The system according to claim 1, characterized in that the measurement means are:
connected to the network of channels, and/or
integrated inside the cell culture chambers.

11. The system according to claim 1, characterized in that the measurement means comprise:
a biomass sensor; and/or
an oxygen sensor, a pH sensor, and/or a $CO_2$ sensor.

12. The system according to claim 1, characterized in that it is a suspension cell culture system suitable for housing inside the chambers cells suspended in culture medium.

13. The system according to claim 1, characterized in that it is a cell culture system by means of the adherence of cells to microparticles or surfaces.

14. A method for culturing cells, characterized in that it is implemented by the suspension cell culture system according to claim 1, and characterized in that it comprises the following steps:
a) introducing cells contained in culture medium inside a first cell culture chamber,
b) circulating the culture medium through the network of channels,
c) transferring the cells contained in culture medium to the inside of a second cell culture chamber,
d) repeating step b) inside the second cell culture chamber,
e) obtaining the cultured cells;
wherein the method further comprises monitoring the state of the cell culture and/or cells through the measurement means in order to determine when the cells achieve certain properties and have to be transferred by means of step c) to a cell culture chamber with a larger internal volume than the one in which they are located, and so on, successively, were it necessary, to chambers of a larger internal volume.

15. The method according to claim 14, characterized in that it comprises conditioning the culture medium through the conditioning means if the measurement means determines that the culture medium is deficient in gases and/or nutrients.

* * * * *